United States Patent [19]

Rogers, Jr.

[11] 4,243,253
[45] Jan. 6, 1981

[54] FLEXIBLE CONDUIT CONSTRUCTION AND METHOD OF MAKING THE SAME

[75] Inventor: Arden D. Rogers, Jr., Knoxville, Tenn.

[73] Assignee: Robertshaw Controls Company, Richmond, Va.

[21] Appl. No.: 6,000

[22] Filed: Jan. 24, 1979

[51] Int. Cl.³ .............................................. F16L 11/12
[52] U.S. Cl. ...................... 285/45; 285/114; 285/226; 285/236; 285/138; 29/446; 29/455 R
[58] Field of Search ............... 285/236, 226, 235, 227, 285/138, 149, 45, 299, 114; 174/13, 86; 138/110, 114, 121, 122, 148; 29/446, 454, 455 R

[56] References Cited

U.S. PATENT DOCUMENTS

| | | | |
|---|---|---|---|
| 592,017 | 10/1897 | McCauley | 285/149 |
| 1,433,537 | 10/1922 | Elliott | 285/149 X |
| 2,300,547 | 11/1942 | Guarnaschelli | 285/149 X |
| 2,344,582 | 3/1944 | Allee | 285/299 X |
| 3,219,365 | 11/1965 | Webb | 285/45 |
| 3,333,871 | 8/1967 | Abbiati et al. | 285/45 |
| 3,369,829 | 2/1968 | Hopkins | 285/227 |
| 3,773,087 | 11/1973 | Katayama | 285/236 X |
| 3,823,249 | 7/1974 | Floessel | 285/45 |
| 4,063,757 | 12/1977 | Fuhrmann | 285/149 |

FOREIGN PATENT DOCUMENTS 124673  7/1947  Australia ................................. 285/120

Primary Examiner—Dave W. Arola
Attorney, Agent, or Firm—Candor, Candor & Tassone

[57] ABSTRACT

A flexible conduit construction having an inner flexible tubular member and having an outer flexible tubular member telescoped about the inner tubular member with the internal peripheral surface of the outer tubular member being in spaced relation from the other peripheral surface of the inner tubular member throughout the length of the inner tubular member to protect the same, a coiled compression spring being disposed about the inner tubular member in spaced relation therewith and radially engaging the internal peripheral surface of the outer tubular member to hold the internal peripheral surface of the outer tubular member in spaced relation relative to the outer peripheral surface of the inner tubular member even though the tubular members are disposed in various arcuately flexed conditions thereof. The outer tubular member is under axial tension between its opposed ends so as to radially contract and thereby be disposed in radial compression against the coiled compression spring.

11 Claims, 7 Drawing Figures

FLEXIBLE CONDUIT CONSTRUCTION AND METHOD OF MAKING THE SAME

BACKGROUND OF THE INVENTION

1. Field of the Invention

This invention relates to an improved flexible conduit construction and to a method of making such a flexible conduit construction or the like.

2. Prior Art Statement

It is known to provide a flexible conduit construction having an inner flexible tubular member and having an outer flexible tubular member telescoped about the inner tubular member with the internal peripheral surface of the outer tubular member being disposed in spaced relation from the outer peripheral surface of the inner tubular member throughout the length of the inner tubular member to protect the same even when the tubular members are in various arcuately flexed conditions thereof.

For example, see the following U.S. patent:

(1) U.S. Pat. No. 3,823,249—Floessel et al

It appears that the flexible conduit section of the conduit construction of item (1) above has an inner tubular bellows construction for permitting flexing of the flexible section and the same is surrounded by a flexible outer tubular member held spaced from the inner bellows construction by a rigid insulator means.

It is also known to protect an inner flexible tubular bellows section by disposing the same within an outer rigid tubular shield member which will permit the bellows construction to be flexed while the outer shield member will remain in a spaced protecting manner about the flexed bellows section.

For example, see the following two U.S. patents:

(2) U.S. Pat. No. 3,219,365—Webb
(3) U.S. Pat. No. 3,369,829—Hopkins

It appears that the flexible conduit sections of items (2) and (3) above each has an outer rigid tubular member disposed in telescoping and spaced relation about an inner bellows construction which permits the conduit section to be flexed and still be protected by the outer rigid tubular member.

SUMMARY OF THE INVENTION

It is a feature of this invention to provide an improved flexible conduit construction which will have an outer protective tubular member disposed about a flexible inner tubular member and will permit the flexible conduit construction to be flexed to various arcuate conditions thereof without requiring the outer tubular member to be unduly large in diameter to permit such arcuate flexing.

In particular, it was found according to the teachings of this invention that when a flexible conduit construction utilized a rigid tubular shield member to protect an inner flexible bellows section or the like, the internal diameter of the outer rigid tubular shield member has to be relatively large to permit the inner tubular member to be flexed to the desired arcuate positions thereof, such as for compensating for misalignment between coupling sections and the like.

It was also found according to the teachings of this invention that if the outer tubular member was also made flexible, such as by merely providing a braided sheath about an inner flexible tubular bellows member as in the U.S. Pat. to Donkle, Jr., No. 3,232,640, the outer sheath would engage the convolutions of the inner flexible bellows member and would transmit impacts thereto so that the outer flexible tubular member would not perform the desired protective function.

However, it was found according to the teachings of this invention that if a resilient means is disposed between the inner flexible tubular member and the outer flexible tubular member, the resilient means will hold the outer flexible tubular member in spaced relation relative to the inner tubular member regardless of the various arcuately flexed conditions of the resulting flexible conduit construction.

In particular, one embodiment of this invention provides a flexible conduit construction having an inner flexible tubular member and having an outer flexible tubular member telescoped about the inner tubular member with the internal peripheral surface of the outer tubular member being in spaced relation from the outer peripheral surface of the inner tubular member throughout the length of the inner tubular member to protect the same, a resilient means being disposed about the inner tubular member in spaced relation therewith and engaging the internal peripheral surface of the outer tubular member to hold the internal peripheral surface in spaced relation relative to the outer peripheral surface of the inner tubular member even when the tubular members are disposed in various arcuately flexed conditions thereof. The outer tubular member has opposed ends and is formed of a material that radially expands when the opposed ends are placed under axial compression and radially contracts when the opposed ends are placed under axial tension. The construction has a pair of end members respectively secured to the opposed ends of the outer tubular member. The resilient means comprises a coiled compression spring having opposed ends respectively secured to the end members. The outer tubular member is under axial tension between the end members and thereby has the internal peripheral surface thereof disposed in radial compression against the coiled compression spring.

Accordingly, it is an object of this invention to provide an improved flexible conduit construction having one or more of the novel features of this invention as set forth above or hereinafter shown or described.

Another object of this invention is to provide a method of making such a flexible conduit construction, the method of this invention having one or more of the novel features of this invention as set forth above or hereinafter shown or described.

Other objects, uses and advantages of this invention are apparent from a reading of this description which proceeds with reference to the accompanying drawings forming a part thereof and wherein:

DESCRIPTION OF THE PREFERRED EMBODIMENTS

Figure 1:
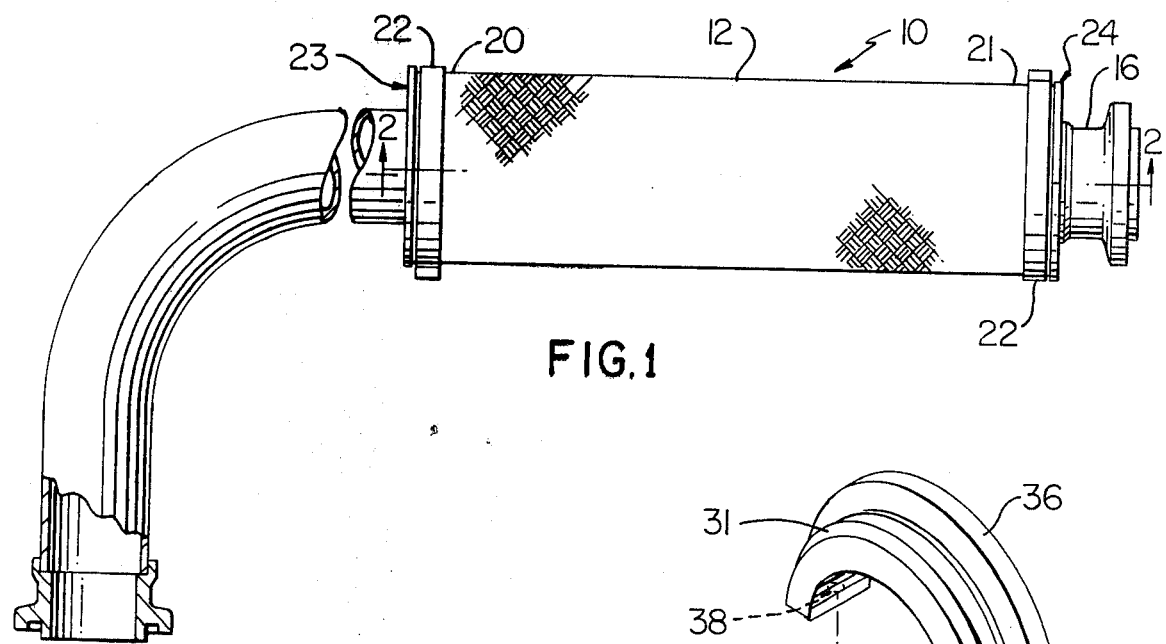
FIG. 1 is a side elevation view of one embodiment of the flexible conduit construction of this invention.

While the various features of this invention are hereinafter described and illustrated as utilizing particular materials for forming the flexible conduit construction, it is to be understood that the various features of this invention can be utilized singly or in any combination thereof with other types of materials, as desired, to provide a flexible conduit construction.

Therefore, this invention is not to be limited to only the embodiments illustrated in the drawings, because the drawings are merely utilized to illustrate one of the wide variety of uses of this invention.

Figure 2:
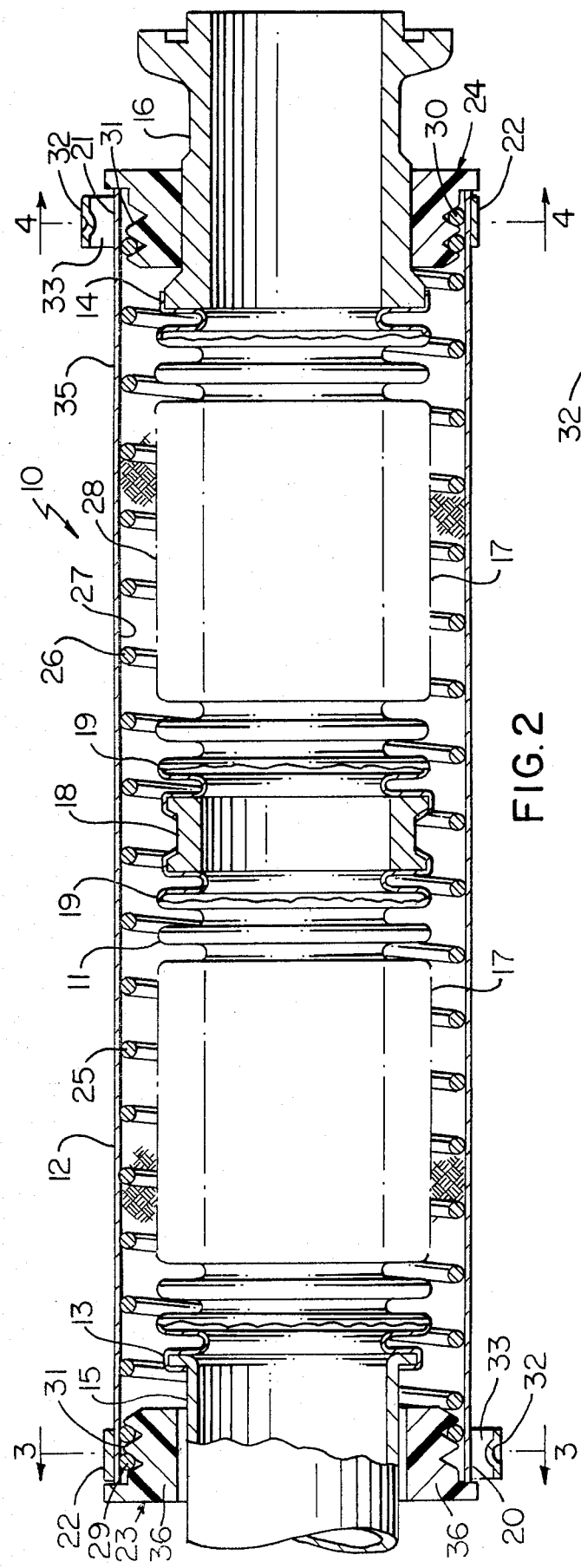
FIG. 2 is an enlarged fragmentary cross-sectional view taken on line 2—2 of FIG. 1.
Figure 4:
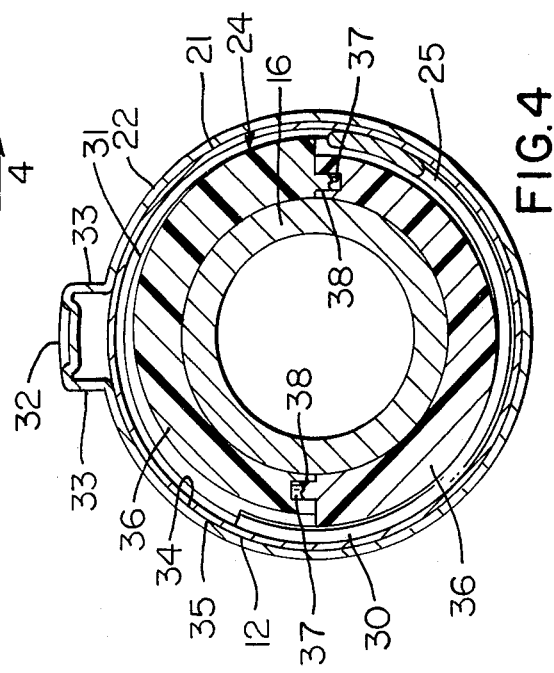
FIG. 4 is a cross-sectional view taken on line 4—4 of FIG. 2.
Figure 3:
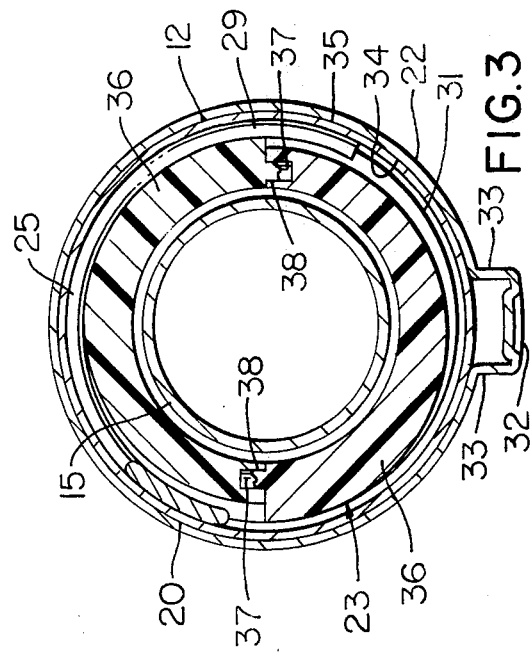
FIG. 3 is a cross-sectional view taken on line 3—3 of FIG. 2.
Figure 5:
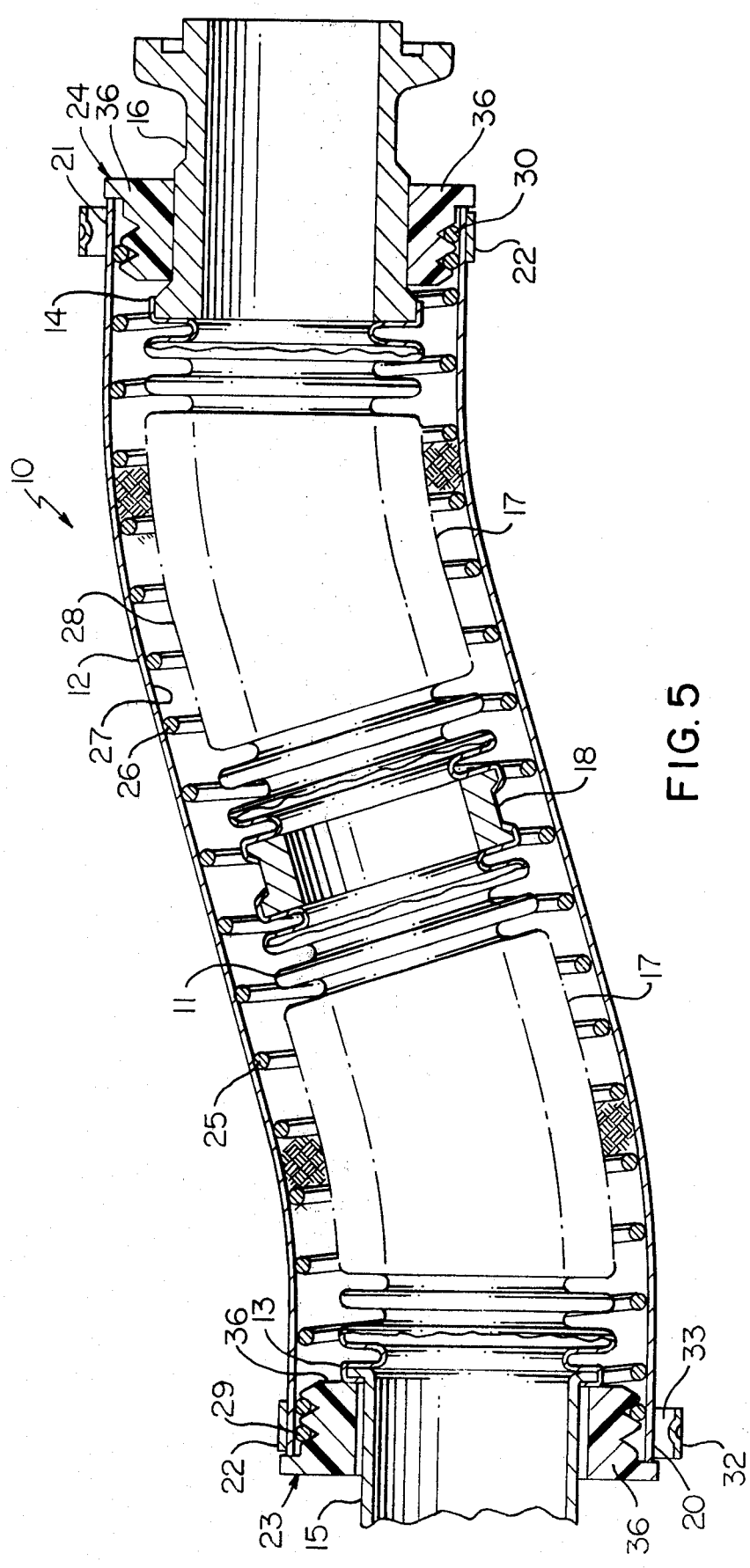
FIG. 5 is a view similar to FIG. 2 and illustrates the conduit construction in an arcuately flexed condition thereof.

Referring now to FIGS. 1 and 2, the improved flexible conduit construction of this invention is generally indicated by the reference numeral 10 and comprises an inner flexible tubular member 11 and an outer flexible tubular member 12 telescoped about the inner tubular member 11, the inner flexible member 11 having the opposed ends 13 and 14 thereof respectively interconnected to rigid coupling members 15 and 16 so that fluid can be passed through the conduit construction 10 from one coupling member to the other for any desired purpose and the tubular members 11 and 12 can be flexed to various arcuate conditions thereof as illustrated in FIG. 5 so as to compensate for any misalignment between the rigid coupling sections 15 and 16 in a particular fluid system utilizing the conduit construction 10.

The inner flexible tubular member 11 can comprise a metallic bellows construction having one or more bellows sections 17 coupled together by ring-like coupling members 18 as illustrated and the outer flexible tubular member 12 can comprise a metallic braided structure as illustrated.

In any event, each bellows section 17 has a plurality of corrugations 19 which are to be protected from impacts or the like by the outer flexible tubular member 12 which can comprise a metallic braided sheath having opposed ends 20 and 21 respectively secured by clamping members 22 to collar-like end members 23 and 24 respectively telescopically disposed on the rigid coupling members 15 and 16.

If desired, the end member 24 can be secured in any suitable manner to its coupling member 16 while the end member 23 remains free to move axially and in telescoping relation on its respective coupling member 15 for a purpose hereinafter described.

A coiled compression spring or resilient means 25 is disposed in telescoping relation about the inner tubular member 17 and in spaced relation therewith so that the individual coils 26 of the spring 25 made contact with the internal peripheral surface 27 of the outer flexible tubular member 12 to hold the internal peripheral surface 27 of the outer flexible tubular member 12 in spaced relation from the outer flexible surface 28 of the inner tubular member 11 throughout the length thereof even when the conduit construction 10 is disposed in various arcuately flexed conditions thereof, such as is illustrated in FIG. 5, whereby the outer flexible tubular member 12 will protect the inner tubular member 11 from external impacts and the like. Thus, the bellows sections 17 will not become damaged and, thus, leak the fluid flowing therethrough or contained therein.

The coiled compression spring 25 has its opposed ends 29 and 30 also secured to the end members 23 and 24. For example, the end members 23 and 24 can have externally threaded sections 31 onto which the ends 29 and 30 of the coiled compression spring 25 can be threaded as illustrated so as to positively secure the ends 29 and 30 of the spring 25 to the end members 23 and 24.

Also, when the clamping members 22 are disposed in telescoping relation on the threaded sections 31 of the end members 23 and 24 and have the sides 32 of the protruding sections 33 thereof inwardly deformed or pinched to pull the internal peripheral surfaces 34 of the respective clamps 22 tightly against the ends 20 and 21 of the outer tubular member 12 to clamp the same against the threaded sections 31 of the end member 23 and 24, one or more end coils 26 of the spring 25 will also be clamped between the teeth of the threaded sections 31. Thus, the opposed ends 29 and 30 of the spring 25 and the opposed ends 20 and 21 of the outer tubular member 12 are positively secured to the end members 23 and 24 by the clamps 22 as illustrated.

However, since the braided tubular member 12 will radially expand when placed under compression between the ends thereof and will radially contract when stretched between the ends thereof, before the clamps 22 are tightened in the manner previously described, the length of the outer tubular member 12 relative to the spring 25 is such that the end members 23 and 24 must be slightly moved axially toward each other after the spring 25 is in place in order to bring the ends 20 and 21 of the outer tubular member 12 into alignment with the ends 29 and 30 of the spring 25. Thus, the spring 25 is placed under slight compression between the end members 23 and 24 so that after the clamps are tightened, the compressed spring 25 elongates and stretches the outer tubular member 12 between its ends 20 and 21 to cause the outer tubular member 12 to radially contract and place its internal peripheral surface 27 into engagement with the outside surface of the coils 26 of the spring 25 even when the conduit construction 10 is in the straight condition illustrated in FIG. 2.

In this manner, it has been found that regardless of the arcuately flexed condition of the tubular members 11 and 12 of the flexible conduit construction 10 of this invention, the compression spring 25 maintains the internal peripheral surface 27 of the outer tubular member 12 in spaced relation from the outer peripheral surface 28 of the inner tubular member 11 so that impacts and the like imparted to the exterior surface 35 of the outer tubular member 12 will not be transmitted to the convolutions 19 of the bellows sections 17 whereby the bellows sections 17 will remain in an undamaged or unweakened condition.

Figure 6:
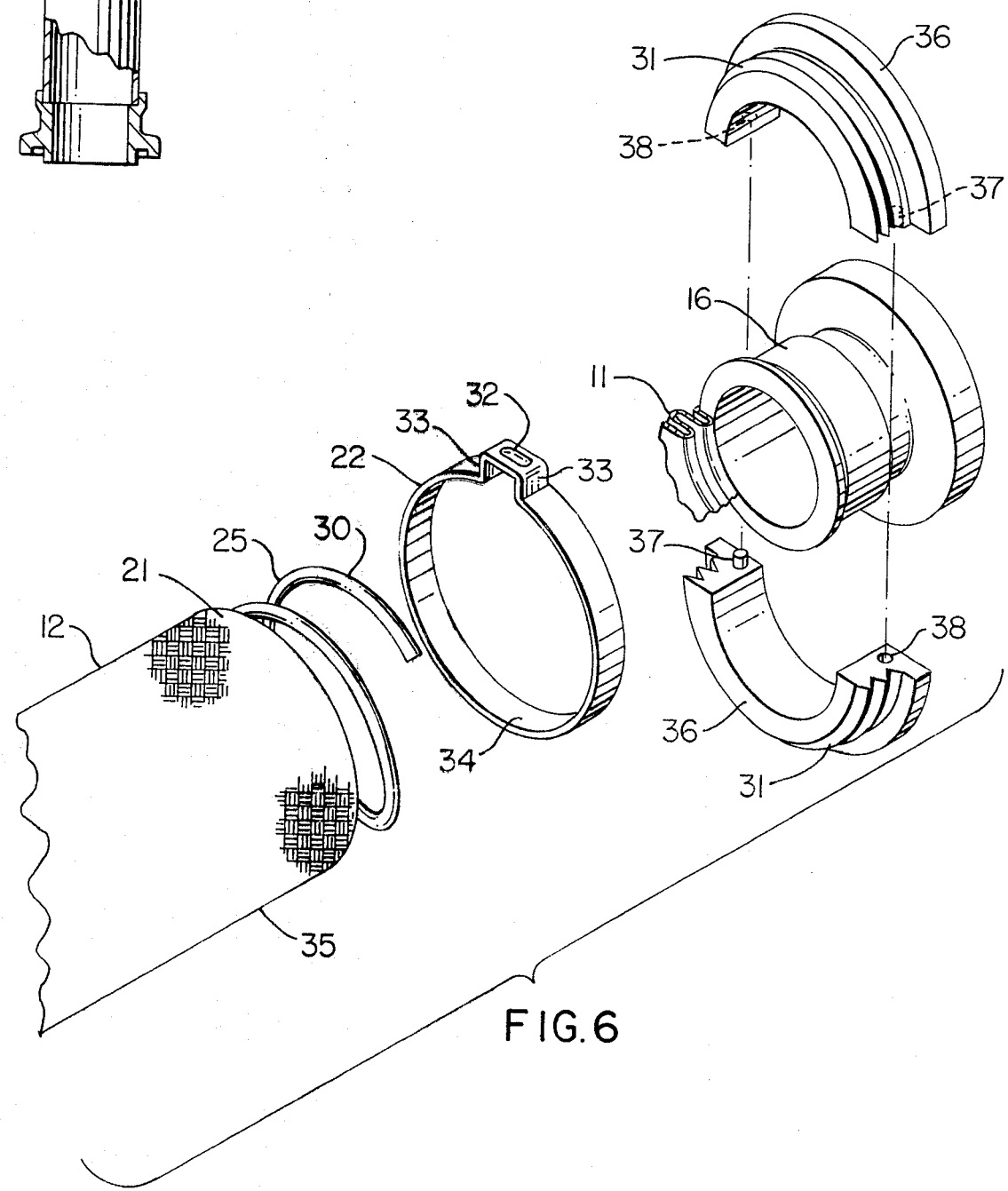
FIG. 6 is a fragmentary, enlarged and exploded perspective view of part of the conduit construction of FIG. 1.

If desired, the end members 23 and 24 can each comprise a pair of split sections 36 as illustrated in FIG. 6 and have cooperating pins 37 and receiving openings 38 so that the cooperating sections 36 can be simply disposed about the couplings 15 and 16 and be held together by the clamping members 22 as illustrated.

Therefore, it can be seen that in the operation of a conduit construction 10 of this invention, the coupling members 15 and 16 can be interconnected to the desired fixed inlet and outlet of a particular fluid system (not shown) and should the couplings 15 and 16 need to be in a misaligned condition from the normal condition illustrated in FIG. 1, the flexible conduit construction 10 can have the inner and outer tubular members 11 and 12 thereof flexed in the manner illustrated in FIG. 5 to permit the coupling members 15 and 16 to be interconnected to the desired structure while the outer flexible member 12 still fully protects the inner flexible tubular member 11 in the manner previously set forth.

Also, during such installation of the conduit construction 10, should it be found that the coupling members 15 and 16 need be closer to each other in an axial direction, or further apart as the case may be, the inner bellows construction 11 permits such shortening or lengthening and the end member 23 will axially move on the coupling member 15 to compensate for the change in length.

If desired, the end member 24 can be secured in any suitable manner to its coupling member 16 and the end member 23 be moved axially to place the braided outer tubular member 12 in compression. This will cause the braided tubular member 12 to radially expand away from the spring 25 which will allow both a compression and an expansion stroke from this position whereby the end of the spring 25 closest to the pivot point of the bellows construction 11 will allow more lateral movement of the assembly before the spring 25 will touch the bellows construction 11.

Figure 7:
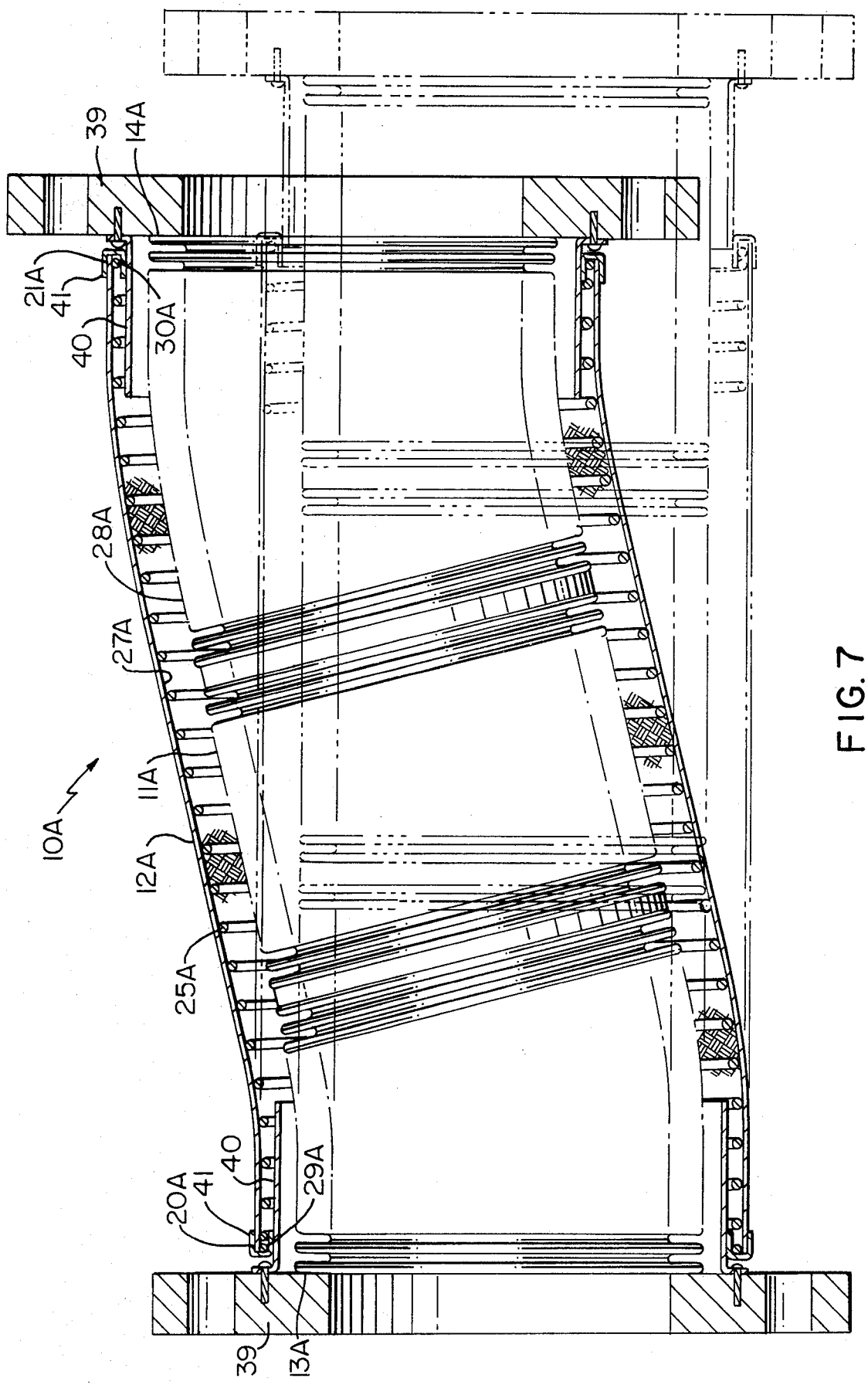
FIG. 7 is a view similar to FIGS. 2 and 5 and illustrates another embodiment of the flexible conduit construction of this invention.

Reference is now made to FIG. 7 where another flexible conduit construction of this invention is generally indicated by the reference numeral 10A and parts thereof similar to the conduit construction 10 previously described are indicated by like reference numerals followed by the reference letter "A".

As illustrated in FIG. 7, the conduit construction 10A includes an outer tubular flexible member 12A disposed in telescoping relation about an inner flexible tubular member 11A and having its internal peripheral surface 27A held in spaced relation relative to the external peripheral surface 28A of the inner tubular member 11A by a coiled compression spring 25A for the reasons previously set forth in regards to the conduit construction 10.

However, the opposed ends 13A and 14A of the inner tubular member 11A are directly fastened to collar-like coupling members 39 which carry axially directed annular sleeves 40 on which the opposed ends 20A and 21A of the outer tubular member 12A are disposed in sliding relation therewith for a purpose hereinafter described.

In particular, the opposed ends 20A and 21A of the outer tubular member 12A and the opposed ends 29A and 30A of the coiled compression spring 25A are fastened together by crimped or deformed annular clamping members 41 which are adapted to telescope onto the sleeves 40 as illustrated to permit the sleeves 40 to be axially moved relative thereto as illustrated between the positions illustrated by the full lines and dash-dotted lines in FIG. 7.

The clamping members 41 also permit the compression spring 25A to be placed under slight compression before the clamping members 41 fasten the opposed ends 20A, 29A and 21A, 30A of the outer tubular member 12A and spring 25A together so that the subsequently contracted outer tubular member 12A will be in engagement with the coils of the spring 25A for the reasons previously set forth.

Therefore, it can be seen that in the operation of the conduit construction 10A, not only are the inner and outer tubular members 11A and 12A adapted to be disposed in various arcuately flexed conditions thereof so as to compensate for misalignment between the coupling members 39, but also the length of the flexible conduit construction 10A can be varied between the coupling members 39 thereof through a sliding relation of one or both sleeves 40 relative to the respective ends of the outer tubular member 12A in the manner previously described.

Accordingly, it can be seen that this invention not only provides an improved flexible conduit construction, but also this invention provides an improved method of making such a flexible conduit construction or the like.

While the forms and methods of this invention, now preferred, have been illustrated and described as required by the Patent Statute, it is to be understood that other forms and method steps can be utilized and still fall within the scope of the appended claims.

What is claimed is:

1. In a flexible conduit construction having an inner flexible tubular member and having an outer flexible tubular member telescoped about said inner tubular member with the internal peripheral surface of said outer tubular member in spaced relation from the outer peripheral surface of said inner tubular member throughout the length of said inner tubular member to protect the same, said outer tubular member having opposed ends and being formed of a material that radially expands when said opposed ends are placed under axial compression and that radially contracts when said opposed ends are placed under axial tension, said construction having end members respectively secured to said opposed ends of said outer tubular member, the improvement comprising resilient means disposed about said inner tubular member in spaced relation therewith and engaging said internal peripheral surface of said outer tubular member to hold said internal peripheral surface in spaced relation relative to said outer peripheral surface of said inner tubular member even when said tubular members are in an arcuately flexed condition, said resilient means comprising a coiled compression spring having opposed ends respectively secured to said end members, said outer tubular member being under axial tension between said end members and thereby having said internal peripheral surface thereof disposed in radial compression against said coiled compression spring.

2. A conduit construction as set forth in claim 1 wherein said inner tubular member comprises a bellows construction.

3. A conduit construction as set forth in claim 1 wherein said flexible tubular member comprises a braided construction.

4. A conduit construction as set forth in claim 1 wherein said inner tubular member has opposed ends, a pair of coupling tubular members respectively secured to said ends of said inner tubular member, said end members having opening means passing therethrough and respectively receiving said pair of coupling members therein.

5. A conduit construction as set forth in claim 4 wherein one of said end members is secured to its respective coupling member.

6. In a method of making a flexible conduit construction having an inner flexible tubular member and having an outer flexible tubular member telescoped about said inner tubular member with the internal peripheral surface of said outer tubular member in spaced relation from the outer peripheral surface of said inner tubular member throughout the length of said inner tubular member to portect the same, said outer tubular member having opposed ends and being formed of a material that radially expands when said opposed ends are placed under axial compression and that radially contracts when said opposed ends are placed under axial tension, said construction having end members respectively secured to said opposed ends of said outer tubular member, the improvement comprising the steps of disposing a resilient means about said inner tubular member in spaced relation therewith and engaging said internal peripheral surface of said outer tubular member to hold said internal peripheral surface in spaced relation relative to said outer peripheral surface of said inner tubular member even when said tubular members are in an arcuately flexed condition, forming said resilient means to comprise a coiled compression spring having opposed ends, securing said opposed ends of said spring respectively to said end members, and placing said outer tubular member under axial tension between said end members and thereby have said internal peripheral surface thereof disposed in radial compression against said coiled compression spring.

7. A method as set forth in claim 6 and including the step of forming said inner tubular member as a bellows construction.

8. A method as set forth in claim 6 and including the step of forming said outer flexible tubular member as a braided construction.

9. A method as set forth in claim 6 and including the steps of securing a pair of coupling tubular members respectively to the opposed ends of said inner tubulr member, and telescopically disposing said end members respectively on said pair of coupling members.

10. A method as set forth in claim 9 and including the step of securing one of said end members to its respective coupling member.

11. A method as set forth in claim 6 wherein said step of placing said outer tubular member under axial tension comprises the step of first securing said opposed ends of said spring respectively to said end members, moving said end members axially toward each other to a position thereof that places said spring under axial compression, holding said end members in said position thereof, and, thereafter, securing said opposed ends of said outer tubular member respectively to said end members while said spring is under said axial compression thereof so that when said end members are released from said position thereof, said spring axial expands to place said outer tubular member under axial tension and thereby have said internal peripheral surface thereof disposed in radial compression against said coiled compression spring.

* * * * *